(12) United States Patent
Kamigauchi et al.

(10) Patent No.: US 6,291,231 B1
(45) Date of Patent: Sep. 18, 2001

(54) MICROORGANISM PRODUCING TERPHENYL COMPOUNDS

(75) Inventors: Toshiyuki Kamigauchi, Osaka; Ryuji Suzuki, Nara, both of (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/551,617

(22) Filed: Apr. 17, 2000

Related U.S. Application Data

(62) Division of application No. 09/142,215, filed as application No. PCT/JP97/01261 on Apr. 11, 1997, now Pat. No. 6,087,540.

(30) Foreign Application Priority Data

Apr. 22, 1996 (JP) ................................... 8-126582

(51) Int. Cl.$^7$ ........................................ C12N 1/14
(52) U.S. Cl. .................. 435/254.3; 435/256.1; 435/913
(58) Field of Search ................ 435/156, 256.1, 435/254.3, 913

(56) References Cited

U.S. PATENT DOCUMENTS 3,632,477 * 1/1972 Dorking et al. .................. 195/81

OTHER PUBLICATIONS

Chemical Abstract No. 123:32830 (1995).
Chemical Abstract No. 108:110096 (1987).
Chemical Abstract No. 102:199272 (1985).
Chemical Abstract No. 92:141619 (1979).
Chemical Abstract No. 91:87011 (1979).
Chemical Abstract No. 88:184469 (1978).
Chemical Abstract No. 85–59292 (1976).
Chemical Abstract No. 83:93558 (1975).
Chemical Abstract No. 80:101133 (1974).
Chemical Abstract No. 79:134223 (1973).
Chemical Abstract No. 66:55421 (1966).
Kobayashi et al., Agric. Biol. Chem., 49 (3), pp. 867–868 (1985).
Kurobane et al., The Journal of Antibiotics, vol. XXXII, No. 6, pp. 559–564 (1979).
Takahashi et al., Chem. Pharm. Bull., 24 (4), pp. 613–620 (1976).
Tringali et al., Can J., Chem., vol. 65, pp. 2369–2372 (1987).
Kallitsis et al., Macromolecules, vol. 27, pp. 4509–4515 (1994).
Elix et al., Aust. J. Chem., 48(5), pp. 1049–1053 (1995).
Kakali et al., Journal of Polymer Science: Part A: Polymer Chemistry, vol. 34 pp. 1581–1588 (1996).
Carrasco, Biochimie, 69(8), pp. 797–802 (1987).
Kobayashi et al., Agric. Biol. Chem., 49(3), pp. 867–868 (1985).
Cutler et al., Proc. Plant. Growth Regul. Work. Group, 6$^{th}$ pp. 87–91 (1979).
Cutler, et al., J. Agric. Food Chem., 26(3), pp. 632–635 (1978).
Marchelli et al., J. Antibiot., 28(4) pp. 328–331 (1975).
Andreeti et al., Cryst. Struct. Commun. 3(1), pp. 145–149 (1974).
Marchelli et al. J. Chem. Soc. Chem. Commun. (15), pp. 555–556 (1973).
Gripenberg et al., Acta Chem. Scand., 20(8), pp. 2202–2206 (1966).

* cited by examiner

*Primary Examiner*—Rosalynd Keys
(74) *Attorney, Agent, or Firm*—Birch, Stewart, Kolasch & Birch, LLP

(57) ABSTRACT

The present invention is a microorganism which is *Aspergillus candidus* RF-5762 (FERM BP-5882), wherein said microorganism is capable of producing a compound of the following formula (I):

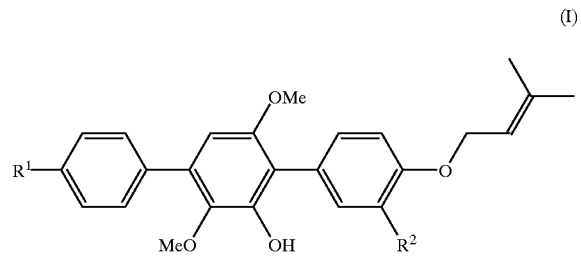

wherein $R^1$ is hydrogen or hydroxy and $R^2$ is hydroxy or methoxy.

1 Claim, No Drawings

MICROORGANISM PRODUCING TERPHENYL COMPOUNDS

This application is a Divisional Under 37 C.F.R. 1.53(b) of application Ser. No. 09/142,215, now U.S. Pat. No. 6,087,540, filed on Sep. 3, 1998. Application Ser. No. 09/142,215 is the national phase under 35 U.S.C. §371 of prior PCT International Application No. PCT/JP97/01261 which has an International filing date of Apr. 11, 1997 which designated the United States of America, the entire contents of which are hereby incorporated by reference.

TECHNICAL FIELD

The present invention relates to a compound which is useful as a pharmaceutical ingredient, a process for producing the same and use of the same. Specifically, a novel terphenyl compound which has an immunosuppressive, antiinflammatory and antitumor activity, a process for producing the same and an immunosuppressive, antiinflammatory and antitumor agent which comprises the same are provided.

BACKGROUND ART

A transplantation of a tissue or an organ which is frequently performed in recent years is attracting attention as a method for recovering a dysfunctional organ or tissue. However, a rejection symptom for excluding a transplanted part after an operation is a serious problem and it is not going too far to say that a success of the transplantation depends on prevention of the rejection symptom.

In these situations, an immunosuppressive agent is being used for prevention and a treatment of a rejection symptom against a transplantation of an organ or a tissue or a graft-versus-host reaction which is caused by a bone marrow transplantation and is an important pharmaceutical agent. The immunosuppressive agent is often used for treating not only a rejection symptom caused by a transplantation but also autoimmune diseases such as chronic rheumatoid arthritis, allergic diseases and the like. Recently, various immunosuppressive agents such as azathioprine, corticoid, cyclosporin A, tacrolimus and the like are developed and clinically used but they are not so satisfactory in view of their effect and side effect.

Many antitumor agents are also clinically used, but most of them have both a potent antitumor activity and toxicity as a side effect, which limits the dosage.

In these situations, a development of an immunosuppressive or antitumor agent which has a potent activity and can safely be used has been desired.

The compounds which belong to the same type as the compounds of the present invention are described in Chemical Pharmaceutics Bulletin, 24 (4), 613–620 (1976), The Journal of Antibiotics, 32 (6), 559–564 (1979), Agricultural Biological Chemistry, 49 (3), 867–868 (1985) and the like. In these literature, these compounds are indicated to have a toxicity against sea urchin embryo cells and Hela cells but their immunosuppressive and antiinflammatory activity are not mentioned at all.

DISCLOSURE OF INVENTION

An object of the present invention is to provide a novel compound which has an immunosuppressive, antiinflammatory or antitumor activity, a process for producing the same and an immunosuppressive, antiinflammatory or antitumor agent comprising the same.

The present inventors found a compound which has a potent immunosuppressive, antiinflammatory and antiproliferative activity on tumor cells in a culture broth of *Aspergillus candidus* RF-5762, a kind of filamentous fungus, isolated and purified the active compound and accomplished the present invention.

The present invention provides a compound of the formula (I):

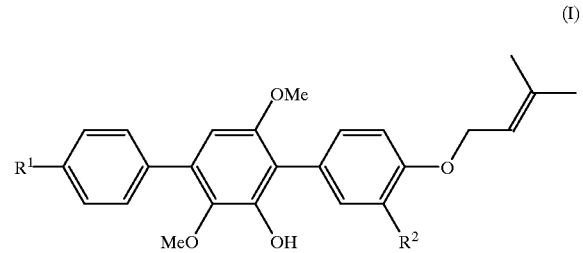

(I)

wherein $R^1$ is hydrogen or hydroxy and $R^2$ is hydroxy or methoxy, pharmaceutically acceptable salts or hydrates thereof. The present invention provides a process for producing the compound (I) which comprises cultivating a microorganism which belongs to the genus Aspergillus and can produce the compound (I) and collecting the compound (I) from the obtained culture. Furthermore, the present invention provides the process for producing the compound (I) which comprises a compound of the formula (II), a precursor of the compound (I):

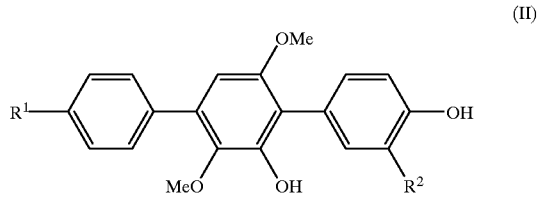

(II)

wherein $R^1$ and $R^2$ are the same as defined above is subjected to a reaction of 3-methyl-2-butenylation.

In an other embodiment, the present invention provides a pharmaceutical composition, specifically, an immunosuppressive, antiinflammatory or antitumor agent comprising the compound (I). Furthermore, the present invention provides a method for suppressing an immune reaction, treating or preventing inflammation or treating tumor which comprises administering the compound (I). Another object of this invention is to provide the use of the compound (I) for the manufacture of a medicament for suppressing an immune reaction, treating or preventing inflammation or treating tumor. Furthermore, the present invention relates to a microorganism which belongs to *Aspergillus candidus* and produces the compound (I).

BEST MODE FOR CARRYING OUT THE INVENTION

A process for producing the compound (I) of the present invention by cultivating a microorganism and by a chemical synthesis is as follows.

A Process by Cultivating a Microorganism

In the present process by cultivating a microorganism, the compound (I) is isolated by the method that a microorganism which can produce the compound (I) of the present invention is cultivated in such a medium composition and under such a condition as being used in usual fermentation production and the fermentation products are separated and collected in a usual manner.

The microorganism which can produce the compound (I) of the present invention includes a fungus which belongs to the genus Aspergillus, for example, *Aspergillus candidus* RF-5762. The morphological character of *Aspergillus candidus* RF-5762 is as follows.

Colonies of this strain on a Czapek's agar medium are white or yellowish white and flat. Their margins are jagged.

A production of a conidial head is good and the reverse side of the colony is colorless or yellowish white. Sometimes this strain produces a brown pigment in an agar. The conidial head is flat spherical in shape of 150–250 μm in diameter and torn to branch later. At the same time a small conidial head of 25–50 μm in diameter is shaped.

Conidiophores are 20–300 μm in length and 4.0–6.0 μm in diameter, their wall are thin and they have dissepiments.

A vesicle is spherical or flat spherical in shape and 13.0–15.0×13.0–15.0 μm. In the surface a metula is formed but in that of a small conidial head it is not formed and the conidial head becomes penicillus.

A metula is 3.5–4.5×6.5–7.5 μm and sometimes becomes hypertrophic to be spherical or pear-shaped and 10.0–14.0× 10.0–14.0 μm in size.

A phialide is 1.5–2.5×4.0–8.0 μm in size. A conidium is spherical of 2.5–4 μm in diameter and the surface is smooth.

Growth temperature is 14° C.–36° C. and optimal growth temperature is 22° C.–32° C.

The above characters were compared with those of known species of the genus Aspergillus described in literature (The genus Aspergillus, 347–350 (1965), Williams&Wilkins; Journal of the Antibacterium and Antifungal Agents, 19(9), 489–495 (1991); Picture book of Fungi (the latter volume), 1006–1045 (1977), Koudan-sya,; Compendium of Soil Fungi Reprint, 1993, 83–85). As a result, the present fungi was identified as *Aspergillus candidus* Link ex Link 1824.

The strain has been deposited under accession No. FERM P-15439 with National Institute of Bioscience and Human Technology (Higashi 1-1-3, Tsukuba, Ibaraki, 305, JAPAN) on Feb. 15, 1996 and then was transferred to the International Deposition under the Budapest Treaty on Mar. 21, 1997 under accession No. FERM BP-5882.

As a medium for producing the present compound (I), either synthetic or natural medium which contains a suitable amount of carbon sources, nitrogen sources and minerals is preferably used. Vitamins or other nutrients may optionally be added if necessary.

Carbon sources to be used are at least one selected from general carbon sources such as sugars such as glucose, maltose, fructose, sucrose, starch and the like, alcohols such as glycerol, mannitol and the like, amino acids such as glycine, alanine, asparagine and the like, organic acids such as gluconic acid, pyruvic acid, acetic acid and the like, fatty acids and glycerides of them such as oleic acid, stearic acid and the like in consideration of the utilization of the microorganism.

Nitrogen sources to be used are at least one selected from organic nitrogenous-compounds such as soybean powder, corn steep liquor, beef extract, peptone, yeast extract, various amino acids and the like and inorganic nitrogenous compounds such as ammonium salts, nitrate salts, and the like in consideration of the utilization of the microorganism.

Calcium carbonate, sodium chloride, potassium chloride, magnesium sulfate, copper sulfate, manganese chloride, zinc sulfate, cobalt chloride or various phosphates may be added as a mineral if necessary.

A deforming agent such as plant oil, lard, polypropylene glycol or the like may be added if necessary.

Addition of solid substance such as crystalline cellulose or pulp to a medium may make the fermentation stable.

The cultivation temperature may be variable as far as the microorganism is allowed to grow and produce the compound (I), however, 15 –30° C. is preferable and 20–26° C. is particularly preferable. Preferable pH is about 6–8, an usual cultivation period is from a few days to a few weeks and the cultivation may be stopped when the production of the compound (I) reaches a plateau. As a method for cultivation any of usual methods such as a solid phase cultivation, aeration-agitation cultivation and the like may preferably be used. In the cultivation step a compound (II), a precursor of the compound (I), can also be produced at the same time.

A method for separating and isolating fermentation product from a culture includes usual methods for separating and purifying fermentation product which is to suitably combine a filtration, a centrifugal separation, an adsorption, a desorption and chromatography with various ion exchange resins or other active absorbents, an extraction with a various organic solvents and the like. For example, a microorganism body separated from a culture is extracted with an organic solvent (ethyl acetate, acetone, methyl ethyl ketone and the like), separated and purified by combination of silica gel chromatography with high performance liquid chromatography.

A Process by a Chemical Synthesis

In the case that an obtained compound by fermentation is a precursor of the compound (I) of the present invention (a compound represented by the formula (II)), the compound may be subjected to a reaction of 3-methyl-2-butenylation to give the compound (I) of the present invention under appropriate conditions.

A precursor is dissolved in an organic solvent such as acetone, dioxane, tetrahydrofuran or the like and a basic catalyst such as a hydroxide or a carbonate of an alkali metal or an alkaline earth metal, a tertiary amine or the like is added to the solution. Examples of the hydroxide or carbonate of an alkali metal or an alkaline earth metal include sodium carbonate, sodium hydrogen carbonate, potassium carbonate, calcium hydroxide, barium hydroxide, calcium carbonate and the like. As the tertiary amine triethylamine and the like are exemplified.

To the obtained solution is added 3-methyl-2-butenyl halide such as 3-methyl-2-butenyl bromide or the like for the selective reaction of 3-methyl-2-butenylation to give the compound (I) of the present invention.

One of the compound (I) of the present invention wherein $R^1$ and $R^2$ are hydroxy in the formula (I) (hereinafter referred to as compound (I-1)) is subjected to alkylation to obtain a compound wherein $R^1$ is hydroxy and $R^2$ is methoxy (hereinafter referred to as compound (I-3)).

Concretely, the compound (I-1) is dissolved in an organic solvent and a basic catalyst such as a hydroxide or a carbonate of an alkali metal or an alkaline earth metal, a tertiary amine or the like is added to the solution. The examples of the organic solvent and the basic catalyst such as a hydroxide or a carbonate of an alkali metal or an alkaline earth metal, a tertiary amine or the like include the same as described above. The compound may be subjected to methylation by adding a methylator such as a methyl sulfate ester such as dimethyl sulfate, benzene sulfate etc. or a methyl halide such as methyl iodide, methyl bromide etc. to the obtained solution.

The present compound (I) includes its formable and pharmaceutically acceptable salts, for example, salts with alkali metals such as sodium, potassium, etc. and with alkaline earth metals such as calcium, barium, etc. The salts may be formed by an usual reaction.

The present compound (I) includes its hydrates and may coordinate to one or more molecules of water per molecule of the present compound (I).

The compound (I) of the present invention has potent immunosuppressive and antiinflammatory activities. It has a suppressive activity of production of cytokines such as IL-2, IL-4 and IL-5, a potent antiproliferative activity on both T and B cells and/or a suppressive activity of antibody production (for example, IgE, IgG, etc., especially IgE) as well as an antiproliferative activity on tumor cell. It may therefore be administered for suppressing an immune reaction, an inflammation or a proliferation of tumor cells as a pharmaceutical composition to animals including human.

The compound (I) of the present invention as an immunosuppressive or an antiinflammatory agent is effective for preventing or treating allergic diseases such as a rejection symptom of an organ or a tissue transplantation, a graft-versus-host reaction caused by a bone-marrow transplantation, allergic diseases (for example, a bronchial asthma, an allergic rhinitis, an allergic dermatitis, an atopy and the like), a high eosinophilic leukocyte syndrome, an allergic conjunctivitis, a systemic lupus erythematosus, a multiple myositis, a skin myositis, a regressive systemic sclerosis, MCTD, a chronic rheumatoid arthritis, an inflammatory bowel disease, an injure by an ischemia-reperfusion, compound (I) is useful as an anticancer agent for treating tumors such as a blood cancer, a solid cancer, etc.

When the compound (I) is administered as a pharmaceutical composition, it can safely be administered both orally and parenterally. In the case of an oral administration, it may be in any usual forms such as tablets, granules, powders, capsules, pills, solutions, syrup, buccal tablets, sublingual tablets and the like. When the composition is parenterally administered, any usual forms are preferable, for example, injections such as intramuscular injection and intravenous injection, a suppository, an endermic agent, a vapor and the like. An oral administration is especially preferable.

A pharmaceutical composition may be manufactured by, if necessary, mixing an effective amount of the compound (I) with various pharmaceutical additives suitable for the form, such as excipients, binders, moistening agents, disintegrators, lubricants and diluents. When the composition is of an injection, an active ingredient can be sterilized with a suitable carrier to give a pharmaceutical composition.

Specifically, examples of the excipients include lactose, saccharose, glucose, starch, calcium carbonate, crystalline cellulose and the like, examples of the binders include methylcellulose, carboxyme pyrrolidone and the like, examples of the disintegrators include carboxymethylcellulose, sodium carboxymethylcellulose, starch, sodium alginate, agar, sodium lauryl sulfate and the like, and examples of the lubricants include talc, magnesium stearate, macrogol and the like. Cacao oil, macrogol, methylcellulose and the like may be used as base materials of suppositories. When the composition is manufactured as solutions, emulsified injections or suspended injections, dissolving accelerators, suspending agents, emulsifiers, stabilizers, preservatives, isotonic agents and the like may be added to it, and when it is manufactured for an oral administration, sweetening agents, flavors and the like may be added.

Although a dosage of the compound (I) as an immunosuppressive agent, an antiinflammatory agent or an anticancer agent should be determined in consideration of the patient's age and body weight, a type and a degree of diseases, and an administration route, an usual oral dosage for human adults is 0.05–100 mg/kg/day and the preferable dosage is 0.1–10 mg/kg/day. In the case that it is parenterally administered, although the dose highly depends on an administration route, an usual dosage is 0.005–10 mg/kg/day and the preferable dosage is 0.01–1 mg/kg/day. The dosage may be administered in one or more separate administrations.

The present invention is further explained by the following Examples, which are not intended to limit the scope of the present invention.

EXAMPLE

Example 1 Separation and Isolation of the Compound (I)

1. Fermentation Process

Fermentation of *Aspergillus candidus* RF-5762: *Aspergillus candidus* which was slant-cultured in a test tube was inoculated in a 500 ml meyer flask containing 100 ml of a medium which comprised 5.0% glucose, 5.0% corn steep liquor, 0.2% calcium carbonate and tap water (pH 7.0, before sterilization) and cultured at 25° C. for 4 days on a rotary shaker at 220 rpm. Each 4 ml of the culture broth was inoculated in twenty 500 ml meyer flasks containing with 100 ml of the fermentation medium which comprised 2.0% glycerol, 2.0% sucrose, 0.3% beef extract, 0.2% yeast extract (pH 7.0%, before sterilization) and cultured at 23° C. for 12 days on a rotary shaker at 180 rpm.

2. Separation and Purification Process

By a filtration under reduced pressure 2 L of the whole broth obtained from the fermentation process was separated into filtrate and mycelial cake. After the mycelial cake was extracted with 500 ml of acetone twice and filtrated under reduced pressure, the filtrate was concentrated under reduced pressure, combined with the former filtrate, extracted with ethyl acetate (pH 6, 500 ml) ×2), washed with water, evaporated for removing a solvent under reduced pressure to give 7.85 g of crude substance. In 30 ml of chloroform 7.85 g of the crude substance was dissolved and subjected to silica gel chromatography (Merck Kieselgel 60, 70–230 mesh, 32 mm i.d.×300 mm). The substance was developed with 300 ml of chloroform and then 400 ml of chloroform:methanol (20:1). Fr. 1–3 (420 ml) containing the compounds (I-1), (II-1), (I-2) and (I-3) were collected and concentrated to a solid under reduced pressure to obtain 0.657 g of partially purified substance.

Fr. 4–7 (280 ml) subsequently eluted contained a compound (II-2) and were concentrated to a solid to obtain 0.577 g of partially purified substance. Then, 1.6 g of a compound (II-3) was obtained from Fr. 8–9 (210 ml) eluted with 400 ml of chloroform:methanol (20:1.5) and 1.46 g of partially purified substance containing a compound (III) was obtained from Fr. 10–12 (160 ml) eluted with 300 ml of chloroform::methanol (20:10) in which an amount of methanol was increased.

2-1. Separation of the Compounds (I-1), (II-1), (I-2) and (I-3)

Fr. 1–3 (0.657 g), partially purified substance containing compounds (I-1), (II-1), (I-2) and (I-3), were subjected to silica gel chromatography (Merck Kieselgel 60, 70–230 mesh, 20 mm i.d.×350 mm) once again. In 5 ml of a development solvent toluene:acetonitrile (85:15) 0.657 g of partially purified substance was dissolved and developed with the same solvent to be separated into 5 g each of fractions. Fr. 13–16 contained the compound (I-2), Fr. 23–26 contained the compound (I-3) and Fr. 27–33 contained the compounds (I-1) and (II-1), and the each fraction was concentrated to a solid to obtain 97 mg, 128 mg and 117 mg, respectively.

2-2. Purification of the Compounds (I-1) and (II-1)

On a silica gel column (Merck Kieselgel 60, 70–230 mesh, 20 mm i.d.×350 mm), 117 mg of the solid containing the compounds (I-1) and (II-1) dissolved in 3 ml of a development solvent toluene:acetonitrile (90:10) was loaded and developed with the same solvent to be separated into 5 g each of fractions. The compounds (I-1) and (II-1) were eluted in Fr. 48–65 (90 ml). The fractions were concentrated to a solid under reduced pressure to obtain a fraction of 90 mg. The obtained was separated and purified by medium-pressured liquid chromatography. A column used was YMC GEL ODS-AM 120-S50, 20 mm i.d.) ×500 mm and a development solvent used was 50% acetonitrile aqueous solution. The fraction eluted at of 594–648 ml contained the compound (II-1) and the fraction at 702–756 ml contained the compound (I-1). Each fraction was collected and concentrated under reduced pressure for removing acetonitrile. The residue was extracted with ethyl acetate, dried over anhydrous sodium sulfate and concentrated to a solid to give 10 mg of pure colorless powders (II-1) and 70 mg of pure colorless powders (I-1). The compound (II-1) was a compound wherein $R^1$ and $R^2$ were hydrogen in the formula (II) and 4"-deoxyterphenilline described in Chemical Pharmaceutics Bulletin, 24(4), 613–620 (1976).

Compound (I-1): $R^1=R^2=OH$; Compound name: 3',6'-dimethoxy-4-(3-methyl-2-butenyloxy)-[1,1':4',1"]terphenyl-3,2',4"-triol; Appearance: colorless prism crystal; Solubility: soluble in acetone, ethyl acetate and chloroform insoluble in water; m. p.: 155.5–156° C.; HR-LSIMS,m/z: calculated for $C_{25}H_{26}O_6$:422.1728; observed: 422.1730 [M]$^+$; LSI-MS, m/z:422[M]$^+$; UV(methanol)nm($\epsilon$): 230(sh), 277(25, 700); 235(sh), 297(26, 200) 0.01 N—NaOH added; 230(sh), 276(24, 500) 0.01 N—HCl added; IRcm$^{-1}$(KBr):3393, 2932, 1611, 1588, 1522, 1490, 1117, 1071, 1001; $^1$HNMR(acetone-d$_6$, 600MHz) δ:1.77(3H,br.s like), 1.79 (3H,br.s like), 3.37 (3H,s), 3.73(3H,s), 4.63(2H,br.d like,J=6.6 Hz), 5.52(1H,m), 6.49(1H,s), 6.83 (1H,dd,J=2.2,8.2 Hz), 6.92(1H,d,J=2.2 Hz), 6.94(2H,m), 6.96(1H,d,J=8.2 Hz), 7.54(2H,m), 7.62(1H,br.s), 7.78(1H,s), 8.64(1H,br.s); $^{13}$CNMR(acetone-d$_6$,150 MHz) δ:18.31(q), 26.00(q), 56.04 (q), 60.67(q), 66.18(t), 103.85(d), 112.75(d), 116.06(d), 117.61(s), 118.97(d), 121.44(d), 123.15(d), 127.91(s), 130.48(s), 130.85(d), 133.54(s), 137.50(s), 140.04(s), 146.23(s), 146.79(8), 149.24(s), 154.51(s), 157.79(s); TLCRf (detected with concentrated sulfuric acid reagent): 0.23; (toluene:acetonitrile=85:15); HPLC: Retention time: 5.6 minutes; Column: YMC-Pack ODS-AM, AM-302, 4.6 i.d.×150 mm (YMC Co., Ltd.); Mobile phase: acetonitrile:water=55:45; Flow rate: 1 ml/minute; Detection: 280 nm(UV).

2-3. Purification of the Compound (I-2)

To medium-pressured liquid chromatography, 97 mg of the solid containing the compound (I-2) was subjected. A column used was YMC GEL ODS-AM120-S5, 20 mm i.d.×500 mm and a development solvent used was 70% acetonitrile aqueous solution. The fraction eluted at 375–435 ml was collected and concentrated under reduced pressure for removing acetonitrile. The obtained residue was extracted with ethyl acetate, dried over anhydrous sodium sulfate and concentrated to a solid to give 70 mg of a pure compound (I-2) as colorless powders.

Compound (I-2): $R^1=H$, $R^2=OH$; Compound name: 3',6'-dimethoxy-4-(3-methyl-2-butenyloxy)-[1,1';4',1"]terphenyl-3,2'-diol; Appearance: colorless powder; Solubility: soluble in acetone, ethyl acetate and chloroform insoluble in water; HR-LSIMS,m/z: calculated for $C_{25}H_{26}O_5$: 406.1779; observed:406.1780 [M]$^+$; LSI-MS,m/z:406 [M]$^+$; UV(methanol) nm($\epsilon$): 225(sh), 274(17,600); 225(sh), 255(sh), 295(26,200) 0.01 N—NaOH added; 225 (sh), 273(18,000) 0.01 N—HCl added; IRcm$^{-1}$(KBr):3506, 3465, 2934, 1585, 1518, 1408, 1116, 1070, 1008; $^1$HNMR (acetone-d$_6$, 600 MHz) δ:1.77(3H,s-like), 1.78(3H,s-like), 3.38(3H,s), 3.73(3H,s), 4.63(2H,br.d-like), 5.53(1H,m), 6.52(1H,s), 6.84(1H, dd, J=2.0, 8.2 Hz), 6.93(1H,d,J=2.0 Hz), 6.97(1H,d,J=8.2 Hz), 7.35(1H,m), 7.44(1H,s), 7.46(2H, m), 7.65(1H,s), 7.66(2H,m); $^{13}$CNMR(acetone-d$_6$, 150 MHz) δ:18.34(q), 26.00(q), 56.26(q), 61.04(q), 66.44(t), 104.45(d), 113.10(d), 118.63(s), 119.07(d), 121.56(d), 123.28(d), 127.96(s), 128.25(d), 129.35(d), 129.84(d), 133.85(s), 137.70(s), 139.65(s), 140.46(s), 146.50(s), 147.07(s), 149.40(s), 154.78(s); TLCRf (detected with concentrated sulfuric acid reagent): 0.54; (toluene:acetonitrile=85:15); HPLC: Retention time: 13.5 minutes; Column: YMC-Pack ODS-AM, AM-302, 4.6 i.d.×150 mm (YMC Co., Ltd.); Mobile phase: acetonitrile:water=55:45; Flow rate: 1 ml/minute; Detection: 280 nm(UV).

2-4. Purification of the Compound (I-3)

After 128 mg of the solid containing the compound (I-3) was dissolved in 1 ml of acetonitrile with heating and the precipitates generated by being allowed at room temperature were removed by filtration, the obtained filtrate was concentrated to a solid to give 35 mg of a residue. The residue was separated and purified by high performance liquid chromatography. A column used was YMC-Pack ODS-AM, 20 mm i.d.×150 mm and a development solvent used was 70% acetonitrile aqueous solution. Fractions of 5 mg each eluted at 72–76 ml were collected to concentrated under reduced pressure and evaporated for removing acetonitrile. The obtained residue was extracted with ethyl acetate, dried over anhydrous sodium sulfate and concentrated to a solid to give 2.7 mg a pure compound (I-3) as colorless powders.

Compound(I-3): $R^1=OH$, $R^2=OCH_3$; Compound name: 3,3',6'-trimethoxy-4-(3-methyl-2-butenyloxy)-[1,1';4',1"]terphenyl-2',4"-diol; Appearance: colorless powder; Solubility: soluble in acetone, ethyl acetate and chloroform insoluble in water; HR-LSIMS, m/z: calculated for $C_{26}H_{28}O_6$:436.1884; observed:436.1880[M]$^+$; LSI-MS,m/z:436 [M]$^+$; UV(methanol)nm($\epsilon$): 230(sh), 278(25,300); 235 (sh), 295(25,100) 0.01 N—NaOH added; 230(sh), 278(24, 500) 0.01 N—HCl added; IRcm$^{-1}$(KBr):3430, 2432, 1612, 1522, 1488, 1398, 1237, 1116, 1075; $^1$HNMR(aceotne-d$_6$, 600MHz) δ:1.77(3H,b.s like), 1.79(3H,br.s like), 3.38(3H, s), 3.74(3H,s), 3.80(3H,s), 4.59(2H,br.d like, J=6.7 Hz), 5.53(1H,m), 6.50(1H,s), 6.93(1H,dd,J=2.0,8.3 Hz), 6.95 (2H,m), 6.97(1H,d,J=8.3 Hz), 6.99(1H,d,J=2.0 Hz), 7.54 (2H,m), 7.83(1H,s), 8.65(1H,s); $^{13}$CNMR(acetone-d$_6$, 150 MHz) δ:18.19(q), 25.84(q), 56.13(q), 56.16(q), 60.65(q), 66.18(t), 104.17(d), 113.80(d), 116.06(d), 116.42(d), 117.70 (s), 121.63(d), 124.37(d), 127.73(s), 130.50(s), 130.79(d), 133.66(s), 137.40(s), 140.17(s), 148.37(s), 149.16(s), 149.98(s), 154.52(s), 157.80(s); TLCRf (detected with concentrated sulfuric acid reagent): 0.34 (toluene:; acetonitrile=85:15); HPLC: Retention time: 7.4 minutes; Column: YMC-Pack ODS-AM,AM-302,4.6 i.d.×150 mm (YMC Co., Ltd.); Mobile phase: acetonitrile:water=55:45; Flow rate: 1 ml/minute; Detection:280 nm(UV).

2-5. Purification of the Compound (II-2)

By silica gel chromatography (Merck Kieselgel 60, 70–230 mesh, 2.4 mm i.d.×200 mm), 0.577 g of partially purified substance containing the compound (II-2) was purified. In 3 ml of toluene:acetonitrile (80:20), 0.577 g of the partially purified substance was dissolved and developed with the same solvent and Fr. 1–3 (120 ml) was collected and concentrated under reduced pressure to give 420 mg of partially purified substance. The obtained residue was separated and purified by medium-pressured liquid chromatography. A column used was YMC GEL ODS-AM120-S50, 20 mm i.d.×500 mm and a development solvent used was 40% acetonitrile aqueous solution. After the fraction eluted at 432–468 ml was collected, the fraction was concentrated under reduced pressure for removing acetonitrile. The residue was extracted with ethyl acetate, dried over anhydrous sodium sulfate and concentrated to a solid to give 90 mg of pure compound (II-2) as colorless powders. The compound (II-2) was a compound wherein $R^1$ is hydroxy and $R^2$ is hydrogen in the formula (II), terphenilline described in Agricultural Biological Chemistry, 49(3), 867–868 (1985).

2-6. Purification of the Compound (II-3)

In methanol (6 ml), 1.6 g of the partially purified substanve containing the compound (II-3) was dissolved. Norit SX-3 (Wako Pure Chemical Industries, Ltd.) (80 mg) was added to the solution and it was stirred for an hour at room temperature. Norit was removed by filtration, water (14 ml) was added and a precipitate generated was dissolved with heating followed by being left at room temperature overnight. The colorless needle crystal generated was filtrated to obtain 1.0 g of the pure compound (II-3). The compound (II-3) was a compound wherein $R^1$ and $R^2$ are both hydroxy in the formula (II), 3-hydroxyterphenilline described in Agricultural Biological Chemistry, 49 (3), 867–868 (1985).

2-7. Purification of the Compound (III)

By silica gel chromatography (Merck Kieselgel 60, 70–230 mesh, 2.4 mm i.d.×200 mm), 1.46 g of the partially purified substance containing the compound (III) was purified. In 12 ml of toluene:acetonitrile (80:20), 1.46 g of the partially purified substance was dissolved and developed with the same solvent. Fr. 4–8 (200 ml) were collected and concentrated under reduced pressure to give 800 mg of pure compound (III) as colorless powders. The compound (III) was 3,3"-dihydroxylterphenilline described in Agricultural Biological Chemistry, 49(3), 867–868 (1985).

Example 2 Synthesis of the Compound (I-1) from the Compound (II-3)

To an acetone solution (5 ml) of 354 mg of the compound (II-3), 402 mg of potassium carbonate anhydride and 149 mg of prenyl bromide were added with 2 ml of acetone and stirred at room temperature for six hours. After insoluble substance was removed by filtration, the filtrate was concentrated under reduced pressure to obtain crude product. The crude product was subjected to medium-pressured column chromatography (column: YMC-GEL ODS-AM 120-S5, 20 mm i.d.×500 mm, solvent: 50% acetonitrile aqueous solution) to be separated into 10 g each of fractions. The compound (I-1) was eluted in Fr. 43–50. After the fractions were concentrated under reduced pressure for removing acetonitrile, the residue was extracted with ethyl acetate, dried over anhydrous sodium sulfate and concentrated to a solid to obtain 138 mg of a pure compound (I-1).

Experiment 1 Suppressive Effect Against in vitro a Mitogen Reaction of Mouse Splenocytes 1-1. Suppressive Effect of a Concanavalin A (Con A) Reaction To each well of a 96 well microtiter plate were added $5 \times 10^5$ BDF1 mouse splenocytes suspended in 0.1 ml of 10% fetal calf serum-fortifed RPMI 1640 medium (2 mM of sodium bicarbonate, 50 units/ml of penicillin, 50 $\mu$g/ml of streptomycin and $5 \times 10^{-5}$ M of 2-mercaptethanol were added) were added. To each well, 5 $\mu$g/ml of Con A as a mitogen and the compound (I-1), (I-2) or (I-3) of a pre-determined concentration were added so that a final volume of each well reached 0.2 ml. Each compound of the present invention was dissolved in dimethylsulfoxide (DMSO) and diluted with the above RPMI 1640 medium to adjust the final concentration to 100 ng/ml or less. The splenocytes in the 96 well microtiter plate were cultivated at 37° C. for 48 hours in an incubator keeping the humidity 100%, carbon dioxide 5% and air 95%. The cells were pulse-labeled with 3H-thymidine (18.5 Kbq/well) before 6 hours of harvest. After the cultivation, the cells were collected by a cell harvester and radioactivity taken in the cells was measured for being used as an indicator of a cell proliferation activity. Con A-free (—Con A) medium was used as a control. The results are shown in Table 1.

TABLE 1

| Compound concentration (ng/ml) | (I-1) Radio-activity cpm ± SD | (I-1) Suppression (%) | (I-2) Radio-activity cpm ± SD | (I-2) Suppression (%) | (I-3) Radio-activity cpm ± SD | (I-3) Suppression (%) |
|---|---|---|---|---|---|---|
| -ConA | 3440 ± 568 | 100 | 3440 ± 568 | 100 | 3440 ± 568 | 100 |
| 0 | 277061 ± 7118 | 0 | 277061 ± 7118 | 0 | 277061 ± 7118 | 0 |
| 0.25 | 292470 ± 542 | −5.6 | 281904 ± 6522 | −1.8 | 285408 ± 7252 | −3.1 |
| 0.98 | 210046 ± 3288 | 24.5 | 281371 ± 10119 | −1.6 | 266173 ± 6208 | 4.0 |
| 3.91 | 56871 ± 1554 | 80.5 | 191575 ± 6969 | 30.9 | 101504 ± 1326 | 64.2 |
| 15.6 | 11366 ± 372 | 97.1 | 41660 ± 531 | 86.0 | 20510 ± 287 | 93.8 |
| 62.5 | 6411 ± 246 | 98.9 | 11793 ± 235 | 96.9 | 7755 ± 624 | 98.4 |
| 250.0 | 6404 ± 403 | 98.9 | 8233 ± 254 | 98.2 | 7522 ± 485 | 98.5 |
| $IC_{50}$ (ng/ml) | 1.2 | | 5.6 | | 2.0 | |

As shown in Table 1, the compounds (I-1), (I-2) and (I-3) significantly suppressed the Con A reaction of mouse splenocytes, depending on the compound concentration.

1-2. Suppression of a Lipopolysaccharide Reaction

By the same method as described in above 1–1 except that lipopolysaccharide (LPS, 10 $\mu$g/ml) was used in spite of concanavalin A, a suppression of the reaction was examined. LPS-free (—LPS) medium was used as a control. The results are shown in Table 2.

TABLE 2

| Compound concentration (ng/ml) | (I-1) Radio-activity cpm ± SD | (I-1) Suppression (%) | (I-2) Radio-activity cpm ± SD | (I-2) Suppression (%) | (I-3) Radio-activity cpm ± SD | (I-3) Suppression (%) |
|---|---|---|---|---|---|---|
| -LPS | 2939 ± 167 | 100 | 2939 ± 167 | 100 | 2939 ± 167 | 100 |
| 0 | 153851 ± 5649 | 0 | 153851 ± 5649 | 0 | 153851 ± 5649 | 0 |
| 0.98 | 153396 ± 6123 | 0.3 | 208023 ± 8941 | −35.9 | 184366 ± 10625 | −20.2 |
| 3.91 | 88405 ± 10394 | 43.4 | 132834 ± 5106 | 13.9 | 128436 ± 4167 | 16.8 |
| 15.6 | 32548 ± 315 | 80.4 | 78686 ± 4135 | 49.8 | 46765 ± 2209 | 71.0 |
| 62.5 | 16070 ± 944 | 91.3 | 39824 ± 651 | 75.6 | 22961 ± 1187 | 86.7 |
| 250.0 | 15046 ± 344 | 92.0 | 22312 ± 1122 | 87.2 | 14962 ± 866 | 92.0 |
| $IC_{50}$ (ng/ml) | 4.5 | | 15.6 | | 8.0 | |

As shown in Table 2, the compounds (I-1), (I-2) and (I-3) have a potent suppressive effect on the LPS reaction of mouse splenocytes which depends on the compound concentration.

Experiment 2 Cell Proliferation Inhibiting Activity of the Compound (I-1)

To each well of a 96 well microtiter plate, the predetermined number of various cell strains (0.1 ml) were added and pre-cultivated for a day under the same cultivation conditions as Experiment 1. To each well, 0.1 ml of the compound (I-1) was added so that the concentration was in the range of 0–10,000 ng/ml. After the cultivation for 3–4 days, 25 μl of 6 mg/ml MTT [3-(4,5-dimethylthiazol-2-yl)-2,5-diphenyltetrazolium bromide] (Sigma) solution was added to each well and the cells were cultivated at 37° C. for 4 hours under the same conditions as above. After the cultivation, 50 μl of 0.02 N hydrochloric acid solution of 20% sodium dodecyl sulfate was added to formazan generated and left at 37° C. for 24 hours for dissolving formazan. An absorption intensity (OD) of formazan generated in proportion to the number of living cells was measured with an immunoreader (InterMed) equipped with a 570 nm filter (The Journal of Immunological Method, No.65, p.55–63, 1983). The 50% inhibitory concentration of a cell proliferation (IC 50) was calculated from a correlation between a concentration of the compound (I-1) and absorption intensity. The results are shown in Table 3.

TABLE 3

| Cell | Origin | Medium[1)] | Cell Number/Well | $IC_{50}$ (ng/ml) |
|---|---|---|---|---|
| CCD-19Lu | human normal pneumocyte | MEM | $2 \times 10^4$ | >10000 |
| Lu-99 | human large cell lung cancer | RPMI 1640 | $2 \times 10^3$ | 1.0 |
| CCFR-CEM | human leukemia cell | RPMI 1640 | $5 \times 10^3$ | 0.2 |
| P388 | mouse leukemia cell | RPMI 1640 | $5 \times 10^2$ | 12.0 |

Medium[1)]: MEM is a medium that 10% fetal calf serum is added to an Eagle's MEM and RPMI 1640 is the same medium as described in Experiment 1 except that a medium for human-derived cells does not contain 2-mercaptethanol.

As shown in Table 3, the compound (I-1) has an antiproliferative activity on the tumor cells but not on the normal pneumocyte CCD-19Lu.

Formulation Example 1

| | |
|---|---|
| The compound (I-1) | 50 mg |
| Lactose | 46 mg |
| Corn starch | 20 mg |
| Low-substituted hydroxypropylcellulose | 8 mg |
| Hydroxypropylmethylcellulose | 5 mg |
| Magnesium stearate | 1 mg |
| Total | 130 mg |

After all of the above ingredients except for hydroxypropylmethylcellulose and magnesium stearate were uniformly mixed, an 8% (w/w) aqueous solution of hydroxypropylmethylcellulose was added to the mixture as binders to give granules for tablet formation by a wet granulation method. These granules were mixed with magnesium stearate and then formed into oral tablets (7 mm diameter and 130 mg per tablet) by a tablet press.

Industrial Applicability

As indicated in the above Experimental Examples, the compound (I) of the present invention has a potent immunosuppressive, antiinflammatory and antiproliferative activity on the tumor cells. The compound (I) of the present invention is very useful for an immunosuppressive, antiinflammatory and anticancer agent.

What is claimed is:

1. A microorganism which is *Aspergillus candidus* RF-5762 (FERM BP-5882), wherein said microorganism is capable of producing a compound of the following formula (I):

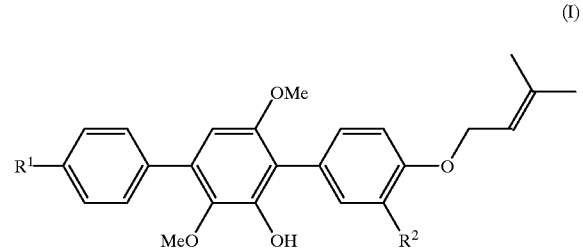

wherein $R^1$ is hydrogen or hydroxy and $R^2$ is hydroxy or methoxy.

* * * * *